US012311201B2

(12) United States Patent
Willis et al.

(10) Patent No.: US 12,311,201 B2
(45) Date of Patent: May 27, 2025

(54) MEDICAL DOSIMETRY SYSTEMS AND METHODS OF USING THE SAME

(71) Applicant: Boston Scientific Scimed, Inc., Maple Grove, MN (US)

(72) Inventors: John Willis, Cork (IE); Conor O'Sullivan, Cork (IE); John Murphy, Cork (IE); Martin Anthony Collier, Cork (IE); Kevin Carbery, Cork (IE); Edward Joseph Devlin, Cork (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 869 days.

(21) Appl. No.: 17/174,188

(22) Filed: Feb. 11, 2021

(65) Prior Publication Data

US 2021/0252312 A1 Aug. 19, 2021

Related U.S. Application Data

(60) Provisional application No. 62/976,209, filed on Feb. 13, 2020.

(51) Int. Cl.
*A61N 5/10* (2006.01)
*A61B 90/00* (2016.01)

(52) U.S. Cl.
CPC ............ *A61N 5/1071* (2013.01); *A61B 90/39* (2016.02); *A61B 2090/374* (2016.02); *A61B 2090/3762* (2016.02); *A61B 2090/3782* (2016.02); *A61B 2090/3925* (2016.02); *A61B 2090/3954* (2016.02); *A61B 2090/3966* (2016.02); *A61B 2090/3995* (2016.02)

(58) Field of Classification Search
None
See application file for complete search history.

(56) References Cited

U.S. PATENT DOCUMENTS

| 6,514,277 B1* | 2/2003 | Lilge | A61N 5/0601 |
| | | | 600/478 |
| 9,936,892 B1* | 4/2018 | Jones | A61B 5/05 |
| 2004/0106891 A1* | 6/2004 | Langan | A61M 25/0084 |
| | | | 604/19 |
| 2005/0059887 A1* | 3/2005 | Mostafavi | A61B 6/032 |
| | | | 600/431 |
| 2009/0131734 A1* | 5/2009 | Neustadter | A61N 5/1049 |
| | | | 600/8 |
| 2010/0036241 A1* | 2/2010 | Mayse | A61B 1/018 |
| | | | 600/435 |
| 2013/0018259 A1* | 1/2013 | Borillo | A61B 90/39 |
| | | | 600/433 |
| 2013/0105692 A1* | 5/2013 | Rink | G01T 1/201 |
| | | | 250/336.1 |
| 2014/0070107 A1* | 3/2014 | Lin | G01T 1/026 |
| | | | 250/370.07 |

FOREIGN PATENT DOCUMENTS

WO WO 2014/165822 * 10/2014 ......... A61N 1/37205

* cited by examiner

*Primary Examiner* — Carrie R Dorna
(74) *Attorney, Agent, or Firm* — Seager, Tufte & Wickhem, LLP

(57) ABSTRACT

A medical device that includes an outer body configured to visually mark a target tissue such that the target tissue is detectable by an imaging system. The medical device includes a sensor disposed within the outer body, wherein the sensor is configured to detect radiation at the target site.

13 Claims, 3 Drawing Sheets

MEDICAL DOSIMETRY SYSTEMS AND METHODS OF USING THE SAME

CROSS-REFERENCE TO RELATED APPLICATIONS

This application claims the benefit of priority from U.S. Provisional Application No. 62/976,209, filed on Feb. 13, 2020, which is incorporated by reference herein in its entirety.

TECHNICAL FIELD

Various aspects of the disclosure relate generally to medical dosimetry systems, devices, and related methods. Examples of the disclosure relate to systems, devices, and related methods for radiographically marking one or more target sites within a patient and detecting a radiation dose therein, among other aspects.

BACKGROUND

Technological developments have given users of medical systems, devices, and methods, the ability to conduct increasingly complex procedures on subjects. One challenge in the field of radiotherapy is associated with providing devices capable of assessing a radiation dose at a target treatment site during a radiotherapy procedure. The limitations of medical devices in providing dose verification at a target treatment site in a patient may prolong the procedure, limit its effectiveness, and/or cause injury to the patient due to overexposure of the tissue to radiation.

SUMMARY

Aspects of the disclosure relate to, among other things, systems, devices, and methods for providing a combined radiographic tissue marker and dose verification system, among other aspects. Each of the aspects disclosed herein may include one or more of the features described in connection with any of the other disclosed aspects.

According to an example, a medical device includes an outer body configured to visually mark a target tissue such that the target tissue is detectable by an imaging system, and a sensor disposed within the outer body, wherein the sensor is configured to detect radiation at the target site.

Any of the medical devices described herein may have any of the following features. The outer body includes a coil and a pair of opposing ends, wherein at least one of the coil and the pair of opposing ends is configured to anchor the outer body to the target tissue. The coil of the outer body includes a linear configuration such that the pair of opposing ends are coaxial relative to one another. The coil of the outer body includes a nonlinear configuration. The coil is configured to form a linear configuration when a radially inward force is applied to the coil, and wherein the coil is configured to transition from the linear configuration to the nonlinear configuration in response to removing the radially inward force from the coil. The coil is a wire wound in a helical configuration. The wire comprises platinum or a conductive metal. The pair of opposing ends of the outer body include atraumatic tips. The sensor is configured to biodegrade. The sensor comprises graphene. The sensor is within a lumen of the coil. The sensor is cylindrical. The imaging system includes at least one of a computed tomography device, an x-ray device, an endoscopic ultrasound device, a cone beam computed tomography device, and a magnetic resonance imaging device. The sensor is fixed relative to the outer body by an adhesive.

According to another example, a medical device includes a coil configured to anchor to a target tissue. The coil comprises a material that is detectable by an imaging system such that the coil is configured to mark a location of the target tissue when positioned at the location. The medical device includes a sensor disposed within and fixed relative to a lumen of the coil. The sensor is configured to detect radiation at the target tissue.

Any of the medical devices described herein may have any of the following features. The coil is selectively deformable from a linear configuration to a nonlinear configuration. The coil includes a wire wound in a helical configuration. The material of the coil includes platinum or a conductive metal. The sensor comprises a biodegradable material such that the sensor is configured to be absorbed by the target tissue. The biodegradable material of the sensor is graphene. The sensor includes a planar sheet deformed to a cylindrical configuration.

According to another example, a medical device includes a first implant including a coiled body and atraumatic ends. At least one of the coiled body and the atraumatic ends is configured to anchor the first implant to a target tissue. The medical device includes a second implant disposed within the coiled body of the first implant. The second implant includes a sensor. The first implant is configured to visually mark the target tissue such that the target tissue is detectable by an imaging system, and the second implant is configured to detect radiation at the target site with the sensor.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
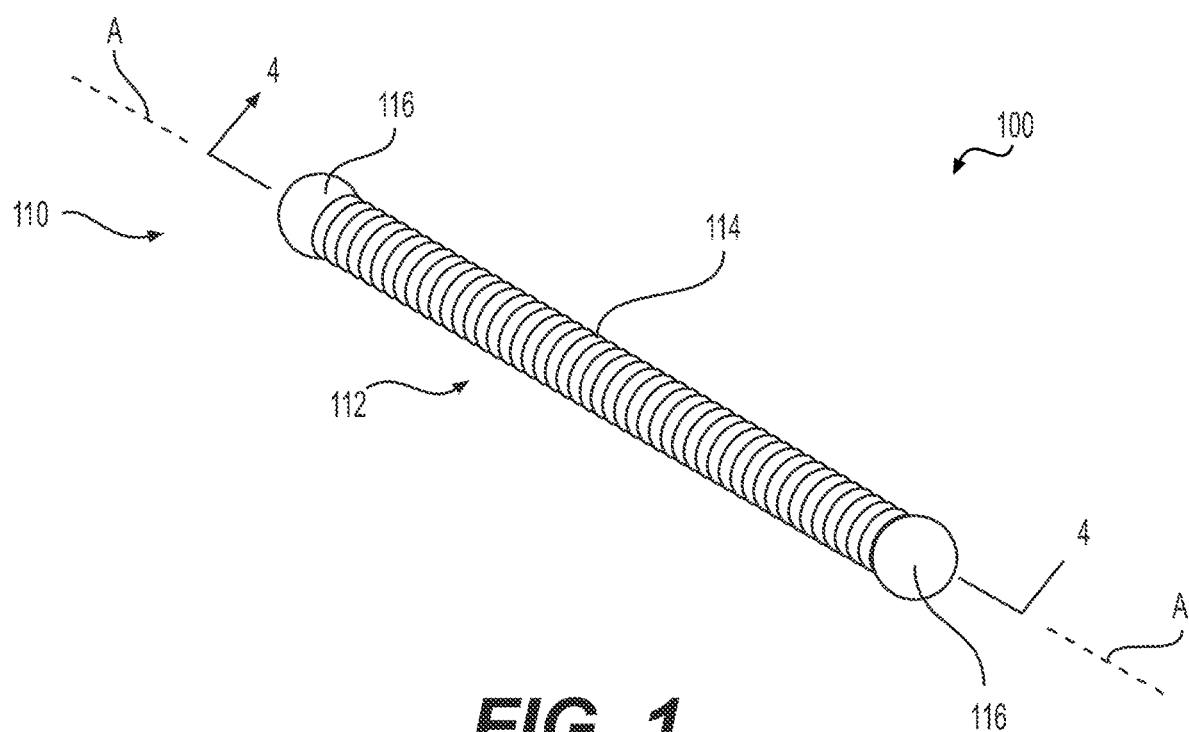
FIG. 1 is a perspective view of an exemplary medical device including a marker device having a linear configuration, according to aspects of this disclosure.

Examples of the disclosure include systems, devices, and methods for radiographically marking one or more target treatment sites within a subject (e.g., patient) and detecting a radiation dose at said one or more target treatment sites. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may be used to mark tissue within a target treatment site for radiotherapy and to measure a radiation dose applied thereto during the radiation therapy procedure. For example, some embodiments may combine a tissue marker with a dosimeter sensor to radiographically mark the tissue within the subject and provide radiation verification of the tissue, during application of radiation doses thereto, respectively. The tissue marker may include a body formed by a coiled wire that extends between opposing atraumatic tips. The coiled wire of the tissue marker may define an inner lumen that is sized and shaped to receive the dosimeter sensor therein. In the examples, the dosimeter sensor may include a body formed by a planar sheet of bioabsorbable material that is selectively deformable from a planar configuration to a nonplanar configuration in accordance with a size and shape of the inner lumen of the tissue marker. The dosimeter sensor may be configured to measure radiation doses delivered to surrounding tissue at a target treatment site.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices. Reference will now be made in detail to examples of the disclosure described above and illustrated in the accompanying drawings. Wherever possible, the same reference numbers will be used throughout the drawings to refer to the same or like parts.

FIG. 1 shows a schematic depiction of an exemplary medical device 100 in accordance with an example of this disclosure. The medical device 100 may include a marker device 110 (e.g., a first/outer body) having a linear coil body 112 extending between a pair of opposing atraumatic ends 116. A longitudinal length of the linear coil body 112 is defined by the pair of opposing atraumatic ends 116. In some examples, the longitudinal length of the linear coil body 112 may range from approximately 4 millimeters (mm) to 6 millimeters (mm), such as, for example, about 5 millimeters (mm). The linear coil body 112 of the marker device 110 is formed of a wire 114 that is wound about a central axis A of the linear coil body 112. An outer diameter of the linear coil body 112 is defined by the wire 114. In some examples, the outer diameter of the linear coil body 112 may range from approximately 0.015 inches (in) to 0.020 inches (in), such as, for example, about 0.018 inches (in).

The wire 114 forming the linear coil body 112 may be formed of a material that is configured and operable to be visually detectable by an imaging system when the marker device 110 is disposed within a subject (e.g., a patient), such as, for example, a computed tomography device, an x-ray device, an endoscopic ultrasound device, a cone beam computed tomography device, a magnetic resonance imaging device, and the like. By way of example, the wire 114 of the linear coil body 112 may be formed of Platinum (Pt), Platinum-Tungsten alloy, and/or various other suitable materials capable of being detected by an imaging system.

In some examples, the pair of atraumatic ends 116 of the marker device 110 may be formed of a similar material as that of the wire 114 and the linear coil body 112. In the example, the pair of atraumatic ends 116 are integrally formed with the linear coil body 112 of the marker device 110 such that each of the atraumatic ends 116 forms a unitary structure with the wire 114 of the linear coil body 112. In other examples, the pair of atraumatic ends 116 may be separate components secured to the linear coil body 112 and/or the wire 114. As described in further detail herein, the marker device 110 may be configured and operable to mark (e.g., radiographically) tissue at a target treatment site within a subject (e.g., a patient).

Still referring to FIG. 1, the linear coil body 112 of the marker device 110 includes a linear configuration such that the pair of opposing atraumatic ends 116 are substantially aligned with one another along the central axis A of the linear coil body 112. A longitudinal length of the linear coil body 112 is coaxial with the central axis A of the linear coil body 112. Further, each of the pair of atraumatic ends 116 of the marker device 110 are coaxial relative to one another and to the central axis A of the linear coil body 112. As described in further detail herein, in other examples, the marker device 110 of the medical device 100 may include various other suitable body configurations and/or shapes than the linear configuration of the linear coil body 112 shown and described herein.

The linear coil body 112 and/or the wire 114 is configured to increase a surface contact of the marker device 110 with an ancillary surface, such as, for example, a tissue at a target treatment site within a subject. The linear coil body 112 and/or the wire 114 may be operable to facilitate anchoring the marker device 110 to tissue at a target treatment site. The pair of atraumatic ends 116 of the marker device 110 may be configured to inhibit injury and/or damage to tissue from the wire 114 when the marker device 110 is positioned within the target treatment site of a subject. In some examples, the pair of atraumatic ends 116 may be sized and shaped to include a diameter that is greater than an outer diameter of the linear coil body 112 and/or the wire 114 of the marker device 110.

The pair of atraumatic ends 116 of the marker device 110 may be further configured to increase surface area of the marker device 110 for contact with an ancillary surface, such as, for example, a tissue at a target treatment site. Accordingly, in addition to and/or in lieu of the linear coil body 112 and/or the wire 114, the pair of atraumatic ends 116 may be operable to facilitate anchoring the marker device 110 to tissue at a target treatment site. In some examples, the pair of atraumatic ends 116 may be configured to receive one or more components of the medical device 100 attached thereto, such as, for example, anchoring devices. Although not shown, it should be appreciated that the pair of atraumatic ends 116 may facilitate and provide a surface for the one or more anchoring devices to attach to the marker device 110.

Figure 2:
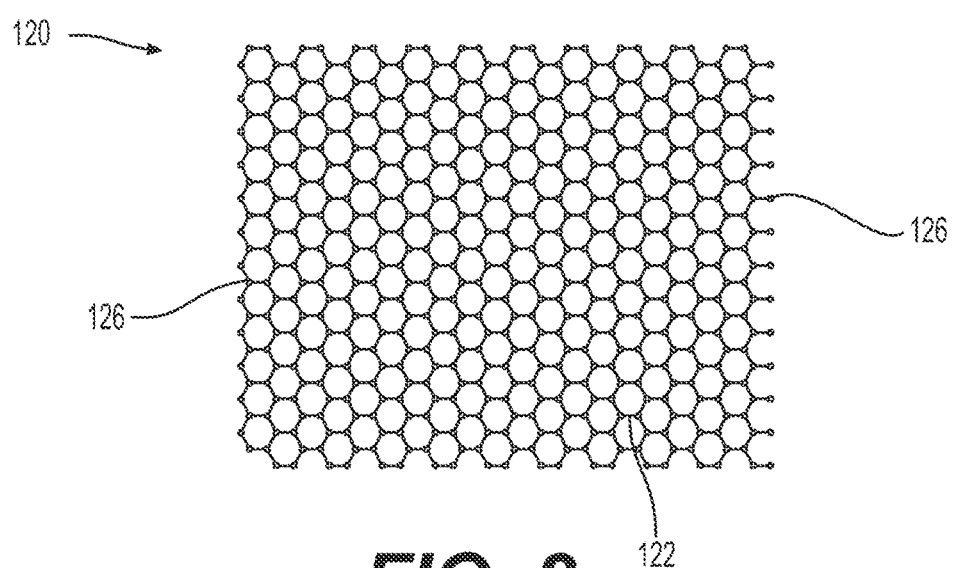
FIG. 2 is a top view of a dosimeter sensor of the medical device of FIG. 1 in a planar configuration, according to aspects of this disclosure.

Referring now to FIG. 2, the medical device 100 may further include a dosimeter sensor 120 (e.g., a second/inner body) having a body 122 extending between a pair of opposing terminal ends 126. In FIG. 2, the body 122 is planar and sheet-like. A longitudinal length of the body 122 is defined by the pair of opposing terminal ends 126. In some examples, the longitudinal length of the body 122 may range from approximately 3 millimeters (mm) to 5 millimeters (mm), such as, for example, about 4 millimeters (mm). The body 122 of the dosimeter sensor 120 includes a plurality of interconnected strands that are woven with another to form a flexible mesh, screen, graft, and/or various other suitable structures. As described in further detail herein, the planer sheet body 122 of the dosimeter sensor 120 may be formed of a flexible, ductile material such that the body 122 is configured and operable to selectively deform to a plurality of sizes, shapes, and/or configurations.

The body 122 of the dosimeter sensor 120 may be comprise bioabsorbable material, so that the body 122 may be biodegradable and/or bioabsorbable. Accordingly, and as described further herein, the dosimeter sensor 120 may be configured and operable to biodegrade within a surrounding material (e.g., tissue) at a target treatment site after the medical device 100 is positioned within a subject (e.g., a patient). In some examples, the body 122 of the dosimeter sensor 120 may be configured such that the dosimeter sensor 120 may be biodegradable and/or bioabsorbable after lapse of a predetermined duration (e.g., day(s), week(s), month(s), etc.) of exposure to the tissue of the target treatment site. By way of example, the body 122 of the dosimeter sensor 120 may be formed of graphene and/or various other suitable materials capable of being biodegradable and/or bioabsorbable within tissue.

Still referring to FIG. 2, and as described above, the body 122 may be formed of a flexible and/or ductile material such that the dosimeter sensor 120 may be configured to flexibly deform to a plurality of configurations and/or shapes. As seen in FIG. 2, the body 122 of the dosimeter sensor 120 may include a planar configuration when in an initial, default state. As described in greater detail herein, the body 122 may be sized and shaped in accordance with a size and shape of the linear coil body 112 of the marker device 110 when the dosimeter sensor 120 is disposed within the linear coil body 112 of the marker device 110. For example, the body 122 may be selectively deformable from the planar configuration to a cylindrical configuration (see FIG. 3) that corresponds to a size and shape of the linear coil body 112 of the marker device 110. In this instance, an outer diameter of the body 122 may range from approximately 0.015 inches (in) to 0.020 inches (in), such as, for example, about 0.017 inches (in). As described in further detail herein, it should be appreciated that an outer diameter of the body 122 may be relatively smaller than an outer diameter of the linear coil body 112 such that the dosimeter sensor 120 may be disposed within the marker device 110.

Figure 3:
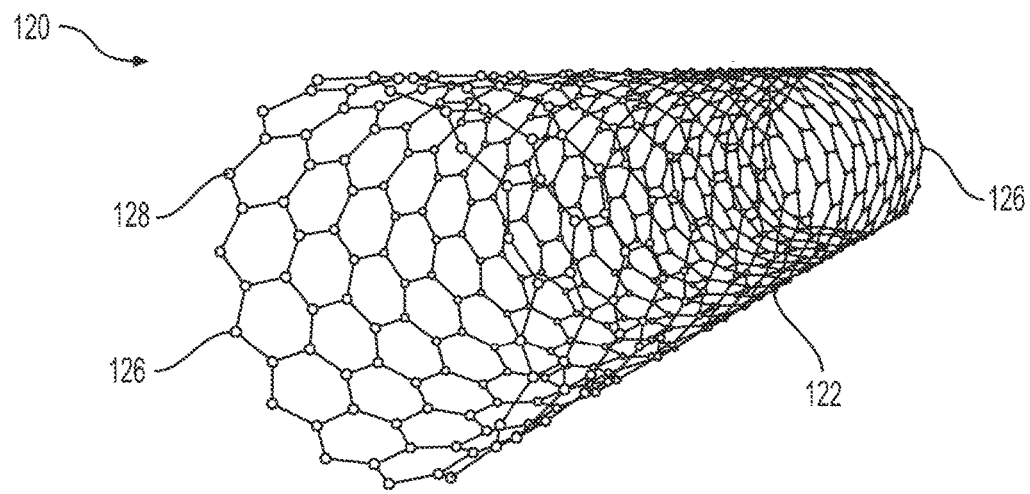
FIG. 3 is a perspective view of the dosimeter sensor of the medical device of FIG. 1 in a cylindrical configuration, according to aspects of this disclosure.

Referring now to FIG. 3, the body 122 of the dosimeter sensor 120 is schematically depicted in the cylindrical configuration. In this instance, the dosimeter sensor 120 of the medical device 100 includes an inner lumen 128 that is defined by an interior surface of the body 122. The inner lumen 128 of the dosimeter sensor 120 extends along a longitudinal length of the body 122, as defined between the pair of opposing terminal ends 126. It should be appreciated that the dosimeter sensor 120 may include various other suitable shapes and/or configurations than those shown and described herein without departing from a scope of this disclosure.

In the example, with the dosimeter sensor 120 formed of graphene, the dosimeter sensor 120 may be configured to sense a voltage change in the presence of an analyte. For example, the dosimeter sensor 120 may be operable to absorb one or more molecules along the body 122 that may alter an electrical conductivity of the dosimeter sensor 120. The change in voltage of the dosimeter sensor 120 may generate a feedback response that is indicative of the molecule(s) received along the body 122. Accordingly, and as described in greater detail below, the dosimeter sensor 120 may detect a radiation dose at a target treatment site in response to encountering radioactive particles, ions, and/or atoms along tissue at the target treatment site.

Figure 4:
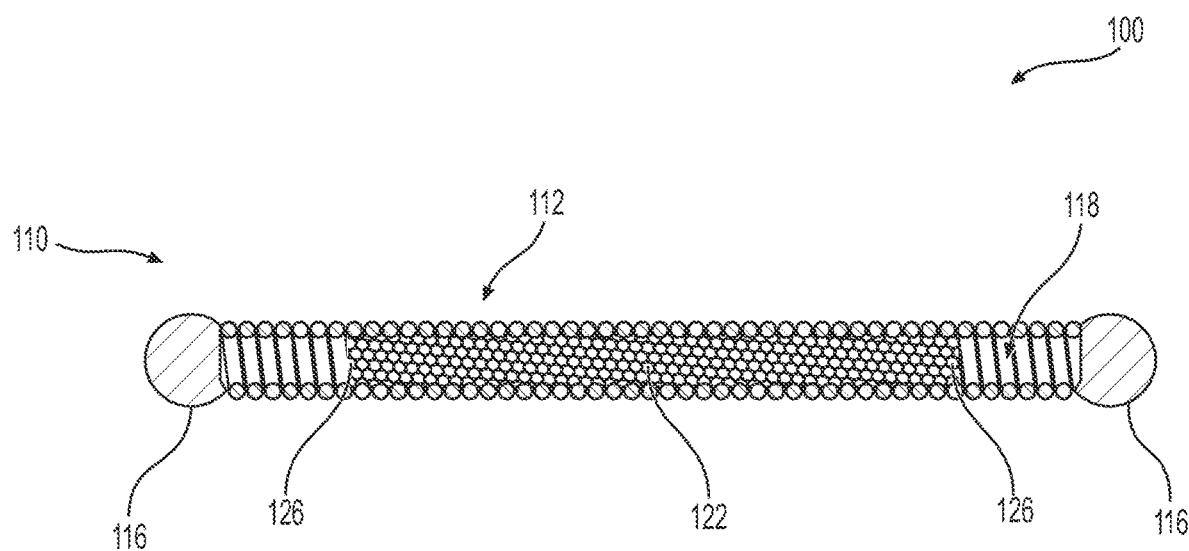
FIG. 4 is a cross-sectional side view of the medical device of FIG. 1 with the dosimeter sensor in the cylindrical configuration and disposed within the marker device, according to aspects of this disclosure.

Referring now to FIG. 4, the medical device 100 is depicted with the dosimeter sensor 120 disposed within the marker device 110. In the example, the linear coil body 112 of the marker device 110 defines a lumen 118 extending between the pair of atraumatic ends 116. The dosimeter sensor 120 may be received within the lumen 118 of the marker device 110 and the body 122 of the dosimeter sensor 120 may be sized and shaped in the cylindrical configuration, in accordance with a size and shape of the lumen 118 of the linear coil body 112.

Figure 5:
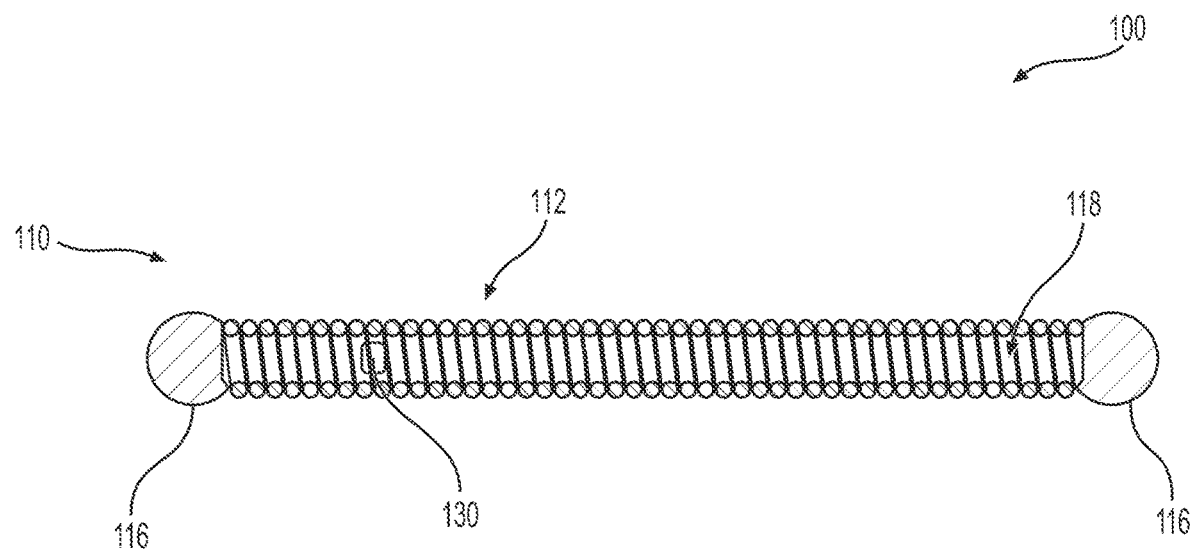
FIG. 5 is a cross-sectional side view of the medical device of FIG. 1 with another dosimeter sensor disposed within the marker device, according to aspects of this disclosure.

Referring now to FIG. 5, in other examples, the medical device 100 may include another exemplary dosimeter sensor 130 in lieu of the dosimeter sensor 120 shown and described above. For example, the dosimeter sensor 130 may be disposed within the inner lumen 118 of the marker device 110 and secured to an interior surface of the linear coil body 112 between the pair of atraumatic ends 116. In this instance, the dosimeter sensor 130 may be fixed to the wire 114 within the inner lumen 118 by an adhesive (not shown), such as, for example, a glue. It should be appreciated that the dosimeter sensor 130 may be positioned within the inner lumen 118 at various positions relative to the atraumatic ends 116 of the linear coil body 112. In other examples, the dosimeter sensor 130 may be positioned along an exterior surface of the linear coil body 112 and/or the wire 114 such that the dosimeter sensor 130 is external of the inner lumen 118.

The dosimeter sensor 130 may be an electrical chip including semiconductor circuitry printed thereon (e.g., a silicon sensor) that is configured and operable to convert changes to a physical parameter into an electrical signal. Accordingly, and as described in greater detail below, the dosimeter sensor 130 may detect a radiation dose at a target treatment site in response to encountering radioactive particles, ions, and/or atoms along tissue at the target treatment site. The one or more circuits of the dosimeter sensor 130 may be further configured and operable to transmit a signal (e.g., via a wireless connection, etc.) indicative of sensor data (e.g., radiation dose measurements) detected by the dosimeter sensor 130 to one or more remote computer stations (not shown) that are communicatively coupled to the dosimeter sensor 130.

By way of illustrative example, the dosimeter sensors 120, 130 shown and described herein may be operable to detect and measure nuclear radiation, electromagnetic radiation, light radiation, and/or various other forms of radiation. In further examples, the medical device 100 may include additional sensors of varying types (positioned on, within, and/or in conjunction with the marker device 110) in addition to and/or in lieu of the dosimeter sensors 120, 130 shown and described above.

Figure 6:
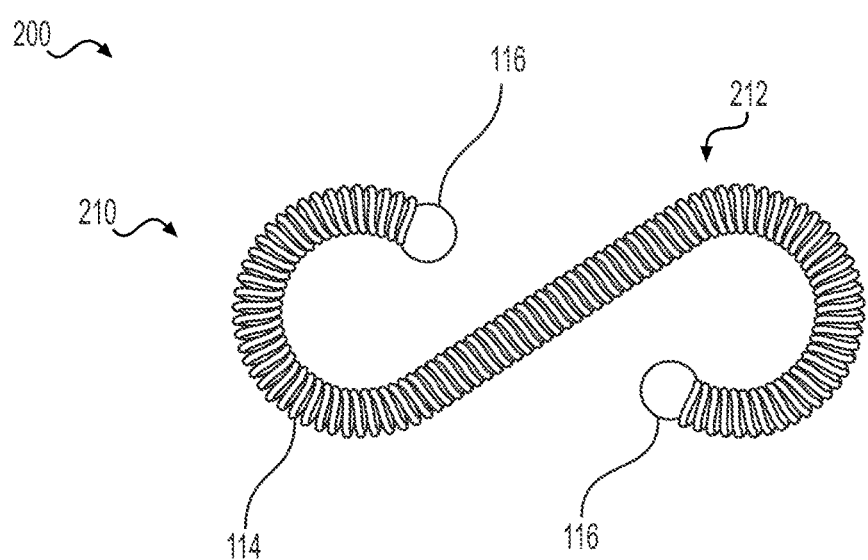
FIG. 6 is a perspective view of another exemplary medical device including a marker device having a nonlinear configuration, according to aspects of this disclosure.

Referring now to FIG. 6, another exemplary medical device 200 is schematically depicted in accordance with an example of this disclosure. Except as otherwise described below, the medical device 200 may be substantially similar to the medical device 100 described above such that like reference numerals are used to identify like components. Accordingly, it should be understood that the medical device 200 may be configured and operable like the medical device 100 except for the differences explicitly noted herein. For example, the medical device 200 may include a marker device 210 having a curved coil body 212 extending between the pair of opposing atraumatic ends 116 and measured along the curved coil body 212. A longitudinal length of the curved coil body 212 is defined by the pair of opposing atraumatic ends 116. In some examples, the longitudinal length of the curved coil body 212 may range from approximately 9 millimeters (mm) to 11 millimeters (mm), such as, for example, about 10 millimeters (mm). The curved coil body 212 of the marker implant 210 is formed of the wire 114 that is wound about the curved coil body 212 in a nonlinear configuration. An outer diameter of the curved coil body 212 is defined by the wire 114. In some examples, the outer diameter of the curved coil body 212 may range from approximately 0.015 inches (in) to 0.020 inches (in), such as, for example, about 0.018 inches (in).

The wire 114 forming the curved coil body 212 may be formed of a material that is configured and operable to be visually detectable by an imaging system when the marker implant 210 is disposed within a subject (e.g., a patient), such as, for example, a computed tomography device, an x-ray device, an endoscopic ultrasound device, a cone beam computed tomography device, a magnetic resonance imaging device, and the like. By way of example, the wire 114 of the curved coil body 212 may be formed of platinum (Pt) and/or various other suitable materials capable of being detected by an imaging system.

In some examples, the pair of atraumatic ends 116 of the marker implant 210 may be formed of a similar material as that of the wire 114 and the curved coil body 212. In the example, the pair of atraumatic ends 116 are integrally formed with the curved coil body 212 of the marker implant 210, and in other examples the pair of atraumatic ends 116 may be separate components secured to the curved coil body 212 and/or the wire 114. As described in further detail herein, the marker implant 210 may be configured and operable to mark (e.g., radiographically) tissue at a target treatment site within a subject (e.g., a patient).

Still referring to FIG. 6, the curved coil body 212 of the marker implant 210 includes a nonlinear configuration such that the pair of opposing atraumatic ends 116 are substantially offset relative to one another. In other words, a longitudinal length of the curved coil body 212 is curved and/or extends along a irregular (nonlinear) configuration, such as, for example, an S-shaped configuration. It should be appreciated that, in other examples, the marker implant 210 of the medical device 200 may include various other suitable configurations and/or shapes than the nonlinear configuration of the curved coil body 212 shown and described herein.

The curved coil body 212 and/or the wire 114 may be configured to increase surface contact of the marker implant 210 with an ancillary surface, such as, for example, tissue at a target treatment site within a subject. The curved coil body 212 and/or the wire 114 may be operable to facilitate anchoring the marker implant 210 to tissue at a target treatment site. Accordingly, the curved coil body 212 and/or the wire 114 may be operable to minimize and/or inhibit migration of the marker implant 210 within a subject (e.g., patient) upon deployment of the marker implant 210 at a target treatment site. It should be understood that the medical device 200 may further include at least one of the dosimeter implants 120, 130 shown and described above. In this instance, the dosimeter implant 120, 130 may be disposed within the curved coil body 212 of the marker implant 210. Accordingly, it should be appreciated that the marker implant 210 of the medical device 200, with the dosimeter implant 120, 130 disposed therein, may be configured and operable similar to the marker device 110 of the medical device 100 described above.

Still referring to FIG. 6, the curved coil body 212 and/or the wire 114 of the marker implant 210 may be selectively deformable such that a shape, configuration, and/or arrangement of the curved coil body 212 may be flexibly adjustable to a plurality of configurations. For example, the marker implant 210 may be configured to deform the curved coil body 212 to a linear configuration, as shown and described above with the linear coil body 112 of the marker device 110 (FIG. 1). In this instance, the curved coil body 212 may be deformed to the linear configuration when, for example, the marker implant 210 is disposed within a linear shaft of a medical instrument (e.g., a delivery needle, sheath, etc.).

The marker implant 210 may be configured to deform in response to application of a radially inward force onto the curved coil body 212 and/or the wire 114 of the marker implant 210. Accordingly, upon deployment of the marker implant 210 from the medical instrument, the curved coil body 212 and/or the wire 114 may return to a preformed shape and/or configuration (e.g., S-shaped configuration) in response to a removal of the radially inward force(s). It should be appreciated that the irregular configuration of the curved coil body 212 of the marker implant 210 may facilitate a visual identification of the marker implant 210 within the target treatment site of the subject through an imaging system, due to an irregularity of a shape of the marker implant 210. In this instance, the medical device 200 may provide improved marking of the target treatment site.

According to an exemplary method of using the medical device 100, 200 to mark a location of a target treatment site within a subject and detect a dose of treatment therapy (e.g., radiation dose) applied thereto, the medical device 100, 200 may initially be positioned at the target treatment site using a medical instrument (not shown). For example, the medical device 100, 200 may be endoscopically implanted at the target treatment site using a medical instrument, such as, for example, any type of endoscope (e.g., duodenoscope, colonoscope, bronchoscope, ureteroscope, etc.). It should be understood that the accompanying description below is not meant to limit the subject matter described herein to a particular method, and that while this disclosure relates to the use of the medical device 100, 200 in a radiotherapy procedure, it should be understood that the features of this disclosure could be used in various other procedures and/or locations (e.g., other organs, tissue, etc.) within a subject's body.

The coil body 112, 212 of the marker device 110, 210 may be operable to anchor the medical device 100, 200 to tissue at the target treatment site. As described in detail above, with the marker device 110, 210 formed of an opaque material (e.g., Platinum) that is operable to be detected by an imaging system, the marker device 110, 210 of the medical device 100, 200 may mark a location of the target treatment site within the subject for visual reference by a user of the medical device 100, 200. In this instance, a user of the medical device 100, 200 may visually identify the location of the target treatment site using an imaging system by detecting the mark provided by the marker device 110, 210.

For example, the marker device 110, 210 may radiographically mark the location of the target treatment site within the subject due to at least one of the coil body 112, 212, the wire 114, and/or the pair of atraumatic ends 116 being formed of Platinum and/or various other suitable materials. Accordingly, a user may improve a targeting accuracy for delivering a treatment therapy (e.g., radiation) to the target treatment site using the medical device 100, 200. With the dosimeter sensor 120, 130 disposed within the inner lumen 118 of the marker device 110, 210, the medical device 100, 200 may further detect radiation doses at the target treatment site. In the example, the dosimeter sensor 120, 130 may be configured and operable to detect and transmit sensor data, including a real-time radiation dose measurement, to a remote computer station (not shown) that is communicatively coupled to the medical device 100, 200 (e.g., via the dosimeter sensor 120, 130).

In some embodiments, the dosimeter sensor 120 may include one or more electrical circuits (not shown) included thereon that are configured and operable to transmit the sensor data described above, such as, for example, by wireless communication to a remote computer station. In other embodiments, the dosimeter sensor 120 may be configured such that a degradation of a material of the dosimeter sensor 120 (e.g., graphene), such as, for example, in response to an exposure to radiation, may be measured and indicative of the sensor data described above. In this instance, the medical device 100, 200 may provide a user with continuous observation of the target treatment site during a procedure (e.g., radiotherapy procedure) by transmitting data relating to measurements of a radiation dose detected from surrounding tissue at the target treatment site. Additionally and/or alternatively, the medical device 100, 200 may transmit measurements of a radiation dose from the target treatment prior to and after completion of a procedure.

In instances where the marker device 110, 210 includes the dosimeter sensor 120 disposed therein, and with the body 122 being formed of biodegradable material, the dosimeter implant 120 may dissolve into the surrounding tissue at the target treatment site after a lapse of a predetermined duration. By way of example, the predetermined duration may range from approximately one or more weeks to one or more months. Accordingly, the medical device 100, 200 may be capable of remaining within the subject at the target treatment site without requiring removal due to a dissolution of the dosimeter sensor 120 after the predetermined duration such that only the marker device 110, 210 may remain at the target treatment site.

Each of the aforementioned systems, devices, assemblies, and methods may be used to mark a location of a target site and detect radiation doses therein. By providing a medical device including a marker implant/device and a dosimeter sensor, a user may accurately identify a location of the medical device at a target site within a subject and detect radiation dose levels from tissue at the target site during a procedure. The medical device may allow a user to reduce overall procedure time, increase efficiency of procedures, and avoid unnecessary harm to a subject's body caused by introducing numerous medical devices into the target treatment site.

It will be apparent to those skilled in the art that various modifications and variations may be made in the disclosed devices and methods without departing from the scope of the disclosure. It should be appreciated that the disclosed devices may include various suitable computer systems and/or computing units incorporating a plurality of hardware components, such as, for example, a processor and non-transitory computer-readable medium, that allow the devices to perform one or more operations during a procedure in accordance with those described herein. Other aspects of the disclosure will be apparent to those skilled in the art from consideration of the specification and practice of the features disclosed herein. It is intended that the specification and examples be considered as exemplary only.

We claim:

1. A medical device, comprising:
an outer body configured to visually mark a target tissue such that the target tissue is detectable by an imaging system, the outer body including a coil and a pair of opposing ends, wherein at least one of the coil and the pair of opposing ends is configured to anchor the outer body to the target tissue; and
a sensor disposed within the outer body, wherein the sensor is a dosimeter sensor that is configured to measure a nuclear radiation dose applied to the sensor at the target site during a radiation therapy procedure;
wherein the coil is configured to form a linear configuration when a radially inward force is applied to the coil, wherein the coil is configured to transition from the linear configuration to a nonlinear configuration in response to removing the radially inward force from the coil, wherein the coil is a wire wound in a helical configuration, and wherein a length of the coil takes on an S-shape nonlinear configuration in response to removing the radially inward force from the coil.

2. The medical device of claim 1, wherein the wire comprises platinum or a conductive metal.

3. The medical device of claim 1, wherein the pair of opposing ends of the outer body include atraumatic tips.

4. The medical device of claim 1, wherein the sensor is configured to biodegrade.

5. The medical device of claim 4, wherein the sensor comprises graphene.

6. The medical device of claim 1, wherein the sensor is within a lumen of the coil.

7. The medical device of claim 6, wherein the sensor is cylindrical.

8. The medical device of claim 1, wherein the imaging system includes at least one of a computed tomography device, an x-ray device, an endoscopic ultrasound device, a cone beam computed tomography device, and a magnetic resonance imaging device.

9. The medical device of claim 1, wherein the sensor is fixed relative to the outer body by an adhesive.

10. A medical device, comprising:
a coil configured to anchor to a target tissue, wherein the coil comprises a material that is detectable by an X-ray imaging system such that the coil is configured to mark a location of the target tissue when positioned at the location; and
a sensor disposed within and fixed relative to a lumen of the coil, wherein the sensor is a dosimeter sensor that is configured to measure a nuclear radiation dose applied to the sensor at the target site during a radiation therapy procedure;
wherein the coil is configured to form a linear configuration when a radially inward force is applied to the coil, wherein the coil is configured to transition from the linear configuration to a nonlinear configuration in response to removing the radially inward force from the coil, wherein the coil is a wire wound in a helical configuration, and wherein a length of the coil takes on an S-shape nonlinear configuration in response to removing the radially inward force from the coil.

11. The medical device of claim 10, wherein the material of the coil includes platinum or a conductive metal, and the sensor comprises a biodegradable material such that the sensor is configured to be absorbed by the target tissue;
   wherein the biodegradable material of the sensor is graphene.

12. The medical device of claim 10, wherein the sensor includes a planar sheet of graphene deformed to a cylindrical configuration.

13. A medical device, comprising:
   a first implant including a coiled body and atraumatic ends, wherein at least one of the coiled body and the atraumatic ends is configured to anchor the first implant to a target tissue; and
   a second implant disposed within the coiled body of the first implant, wherein the second implant includes a dosimeter sensor;
   wherein the first implant is configured to visually mark the target tissue such that the target tissue is detectable by an imaging system, and the second implant is configured to measure a nuclear radiation dose applied to the dosimeter sensor at the target site during a radiation therapy procedure, wherein the coil is configured to form a linear configuration when a radially inward force is applied to the coil, wherein the coil is configured to transition from the linear configuration to a nonlinear configuration in response to removing the radially inward force from the coil, wherein the coil is a wire wound in a helical configuration, and wherein a length of the coil takes on an S-shape nonlinear configuration in response to removing the radially inward force from the coil.

* * * * *